United States Patent [19]

Fujioka et al.

[11] Patent Number: 5,725,714
[45] Date of Patent: Mar. 10, 1998

[54] METHOD FOR MAKING COMPONENTS OF ABSORBENT UNDERGARMENT

[75] Inventors: Yoshihisa Fujioka; Yasushi Sayama, both of Kagawa-ken, Japan

[73] Assignee: Uni-Charm Corporation, Ehime-ken, Japan

[21] Appl. No.: 720,157

[22] Filed: Sep. 25, 1996

[30] Foreign Application Priority Data

Sep. 29, 1995 [JP] Japan .................. 7-253468

[51] Int. Cl.⁶ .............. A61F 13/15; A61F 13/56; A61F 13/58; B32B 31/08
[52] U.S. Cl. .............. 156/259; 156/256; 156/265; 156/302; 604/385.1; 604/389; 604/390
[58] Field of Search .............. 156/259, 256, 156/265, 299, 302, 297; 604/389, 390, 391, 385.1

[56] References Cited

U.S. PATENT DOCUMENTS

| | | |
|---|---|---|
| 3,089,494 | 5/1963 | Schwartz ........................... 604/389 |
| 4,690,719 | 9/1987 | Lucas et al. . |
| 4,760,764 | 8/1988 | De Jonckheere et al. . |
| 4,850,988 | 7/1989 | Aledo et al. ........................ 604/389 X |
| 5,034,007 | 7/1991 | Igaue et al. ..................... 604/385.1 X |
| 5,110,386 | 5/1992 | Ochi et al. ......................... 156/265 X |
| 5,399,219 | 3/1995 | Roessler et al. . |
| 5,453,143 | 9/1995 | Menard ............................ 604/389 X |

FOREIGN PATENT DOCUMENTS

| | | |
|---|---|---|
| 0 396 050 | 11/1990 | European Pat. Off. . |
| 0 539 032 | 4/1993 | European Pat. Off. . |
| 2-291857 | 12/1990 | Japan . |

*Primary Examiner*—Adrienne C. Johnstone
*Attorney, Agent, or Firm*—Lowe, Price, LeBlanc & Becker

[57] ABSTRACT

A disposable undergarment such as a diaper is provided at side edges of side sheets thereof with fastening regions and laterally projecting tabs facilitating the fastening regions to be operated. Simultaneously with obtaining the side sheets having a series of alternating concave and convex edge portions by longitudinally cutting a continuous web along a concave-convex cutting line, second concave and convex edge portions which are alternately repeated and smaller than the first-mentioned concave and convex edge portions are provided utilizing the same cutting line. Of these second concave and convex edge portions, the latter define the tabs.

4 Claims, 4 Drawing Sheets

METHOD FOR MAKING COMPONENTS OF ABSORBENT UNDERGARMENT

BACKGROUND OF THE INVENTION

The present invention relates to a method for making components of an undergarment and particularly to an absorbent undergarment such as disposable diapers, disposable incontinence pads and the like.

It is known in making disposable undergarments to reduce the material cost by a cutting continuous web into first and second partial webs so that each has a series of periodical concave edge portions and a series of periodical convex edge portions with respect to a longitudinal center line of the continuous web and then cutting these first and second partial webs into a predetermined length to obtain components of an individual undergarment, such as in disclosed Japanese Laid-Open Patent Application No. Hei2-291857.

According to this Application, the first partial web is longitudinally shifted relative to the second partial web by a predetermined pitch so that the concave and convex edge portions of the first partial web are exactly aligned with the corresponding concave and convex edge portions of the second partial web, respectively. Outer edges of these first and second partial webs remote from their concave and convex edge portions, respectively, are bonded to respective outer edges of a second continuous web to form a composite web which can be used not only as components of the undergarment such as a topsheet and a backsheet but also as a pressure-sensitive tape fastener of a disposable diaper.

The tape fastener obtained according to the disclosure of the foresaid Application has a base end for securing to a main body of the diaper, a free end serving as a nonadhesive tab and an intermediate portion extending between these two ends, serving as an adhesive fastening means. If the tape fastener can be formed with the foresaid components of the undergarment, a manufacturing cost thereof will be reduced.

From this viewpoint, it is a principal object of the invention to reduce a manufacturing cost of the undergarment by forming tabs functioning as fasteners integrally and simultaneously with a topsheet and/or backsheet as components of the undergarment.

SUMMARY OF THE INVENTION

The object set forth above is achieved, according to the invention, by a method for making components of an undergarment comprising steps of subjecting a first continuous web having side edges to cutting in a longitudinal direction along an alternative concave-convex cutting line between said side edges to thereby form a first partial web and second partial web that each has a series of alternating concave edge portions and a series of alternating convex edge portions, longitudinally shifting the first partial web relative to the second partial web by a predetermined pitch so that the concave and convex edge portions of the first partial web are exactly aligned with the corresponding concave and convex edge portions of the second partial web, respectively, and bonding outer edges of these first and second partial webs remote from their concave and convex edge portions to respective outer edges of a second continuous web to form a composite web, said method being characterized in that said method further comprises steps of utilizing said cutting line to form in said concave and convex edge portions of said first and second partial webs second concave and convex edge portions which are able to be respectively aligned simultaneously as said first and second partial webs are aligned to each other and smaller than the first-mentioned concave and convex edge portions; and forming fastening regions used to fasten said undergarment around the wearer's waist on and/or adjacent said second convex edge portions.

DESCRIPTION OF THE PREFERRED EMBODIMENTS

Figure 1:
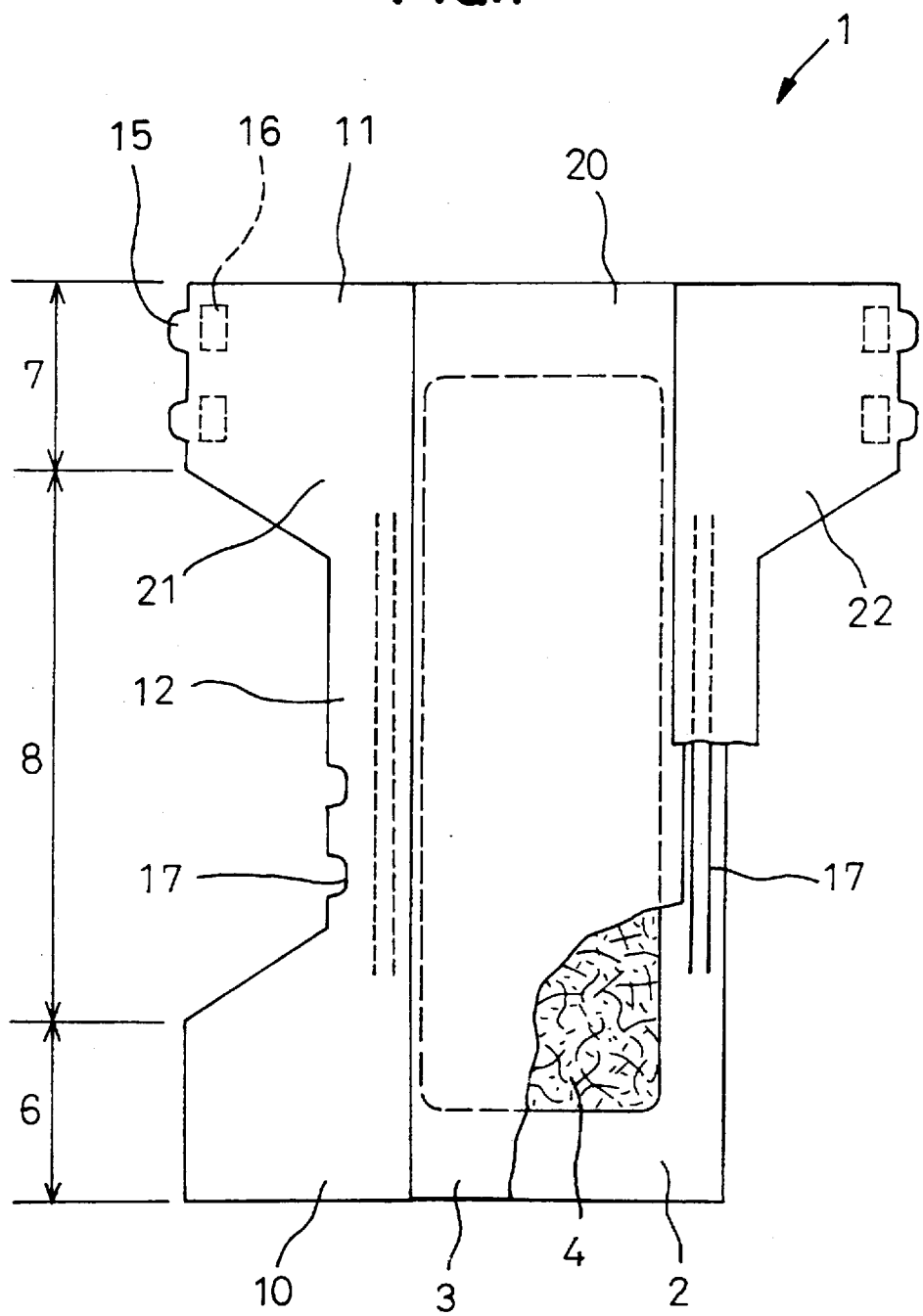
FIG. 1 is a plan view showing an undergarment (disposable diaper) as partially broken away.

FIG. 1 shows a disposable diaper 1 as a specific embodiment of the inventive garment in a plan view as partially broken away and as viewed from its outer side. The diaper 1 comprises a liquid-permeable topsheet 2, a liquid-impermeable composite backsheet 3 and a liquid-absorbent core 4 disposed between these two sheets 2, 3. Portions of these two sheets 2, 3 extending outward beyond a peripheral edge of the core 4 have their inner surfaces bonded together. The diaper 1 has a front section 6, a rear section 7 and a crotch section 8 extending between the two sections 6, 7. Wings 10, 11 extend outward from transversely opposite sides of the front and rear sections 6, 7 and the crotch section 8 is formed along it's transversely opposite sides with cutouts 12 recessed inwardly of the diaper 1 so that these cutouts 12 are adapted to define a pair of leg-openings, respectively. Tabs 15 extend outward from the transversely opposite side edges of the wings 11 associated with the rear section 7. Inner surfaces of these tabs 15 themselves and/or regions adjacent thereto are coated with adhesive to form fastening regions 16. The cutouts 12 are provided with elastic members 17 disposed between the topsheet 2 and backsheet 3 and secured in a stretched condition to the inner surface of at least one of these two sheets 2, 3. The cutouts 12 are formed with relatively small notches 17 which are placed aside toward the front section 6.

The topsheet 2 in the illustrated embodiment is formed of a rectangular nonwoven fabric or perforated plastic sheet which is relatively long in the longitudinal direction of the diaper 1 and the composite backsheet 3 comprises a rectangular middle sheet 20 and side sheets 21, 22 joined to transversely opposite side edges of the middle sheet 20. The middle sheet 20 and the side sheets 21, 22 are preferably air-permeable, more preferably air-permeable and liquid-impermeable. It is also possible to use the air-impermeable middle sheet 20 in conjunction with the air-permeable side sheets 21, 22. Particularly when the core 4 has a sufficiently high water retention capacity, all these sheets 20, 21, 22 may be air-permeable and liquid-permeable. Plastic sheet or nonwoven fabric may be used as material for these sheets 20, 21, 22.

With the diaper 1 constructed as has been described above, the fastening regions 16 are fastened to the outer surface of the front section 6 when the diaper 1 is put on wearer's body. Said fastening regions 16 provided adjacent the base ends of the tabs 15 can be reliably and quickly fastened to the outer surface of the front section 6 merely by holding the tabs 15, even though these tabs 15 are relatively small-sized. The fastening regions 16 once fastened to the outer surface of the front section 6 can be released therefrom merely by holding the tabs 15 without feeling for a position where the fastening regions 16 are.

Figure 2:
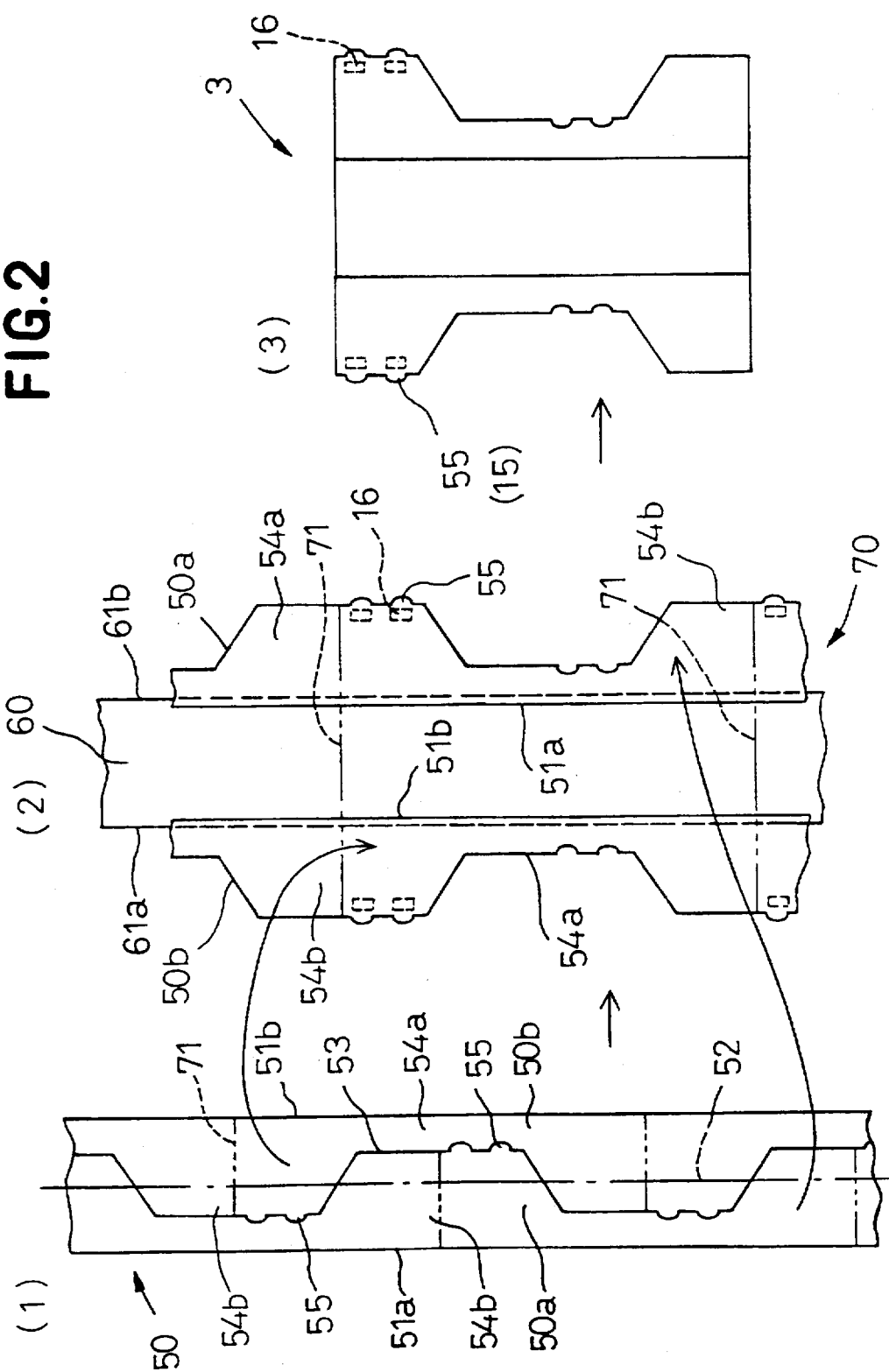
FIG. 2 is a schematic diagram illustrating steps (1), (2) and (3) for making a composite backsheet.

FIG. 2 is a schematic plan view illustrating a method for continuously making the composite backsheet 3. Referring to FIGS. 1 and 2(1), a first continuous web 50 has transversely opposite side edges 51a, 51b which are substantially parallel to each other; with respect to a longitudinal central line 53, an alternating concave-convex cutting line 53 for forming concave-convex portions is drawn in a periodical way along the longitudinal direction, so that the first web 50 is cut along the cutting line 53 to form first and second partial webs 50a, 50b both having a series of alternating concave edge portions 54a and a series of alternating convex edge portions 54b. Referring to FIG. 2(2), the first partial web 50a is longitudinally shifted relative to the second partial web 50b by ½ X n (n: odd number) pitches so that the concave edge portions 54a as well as the convex edge portions 54b are aligned with the corresponding concave edge portions 54a and convex edge portions 54b of the second partial web 50b, and then the first partial web 50a is parallel moved to the right side of the second partial web 50b with the respective concave edge portions 54a and convex edge portions 54b lying outside while straight side edges 51a, 51b lying inside. A second continuous web 60 has its transversely opposite side edges 61a, 61b extending substantially parallel to each other. The first and second partial webs 50a, 50b are placed parallel to each other on body sides of the second web 60, then the straight side edge 51a and region adjacent thereto are put upon and joined to the side edge 61b and region adjacent thereto of the second web 60 while the straight side edge 51b and region adjacent thereto are put upon and joined to the side edge 61a and region adjacent thereto so as to form a continuous composite web 70. The composite web 70 is cut along second cutting lines 71 dividing the respective convex edge portions 54b into upper and lower halves to obtain composite backsheets 3 each having a length required for an individual diaper as shown by FIG. 2(3). The first and second partial webs 50a, 50b respectively have second convex edge portions 55 defined smaller than the convex edge portions 54b below the second cutting line 71. Referring to FIG. 2(1), such second convex edge portions 55 are formed by partially cutting the concave edge portions 54a away to define the tabs 15 of the composite backsheet 3 shown in FIG. 1. In the course of forming the composite backsheet 3 from the first and second partial webs 50a, 50b, adhesive is applied or adhesive tape strips are bonded to the second convex edge portions 55 and/or the regions adjacent thereto to form the fastening regions 16. It is preferred to protect these fastening regions by covering them with a release sheet (not shown).

The cores 4 are disposed between the continuous composite web 70 or the individual composite backsheets 3 obtained in the manner as has been described above and the topsheets 2 supplied continuously or individually to obtain the diapers 1 wherein, in the case of the continuous composite web 70, the assembly obtained after the step of covering the cores 4 with the two webs is successively cut along the second cutting line 71 to obtain the individual diapers 1.

As will be apparent from FIG. 1 or FIG. 2(3), the second convex edge portions 55 (i.e., tabs 15) are formed merely by cutting small portions away from the side edges 12 of the crotch section 8 without requiring any separate members. While such cutouts practically affects a feeling to wear the diaper 1, the topsheet 2 may be enlarged until its transversely opposite side edges reach the side edges of the core 4 in the crotch zone 8 to avoid any stimulus to the wearer's skin due to the presence of these cutouts.

Without departing from the scope of the invention, the topsheet 2 may be subjected to the step as illustrated in FIG. 2, instead of the composite backsheet 3 exemplarily shown in FIGS. 1 and 2 and thus the topsheet 2 may be formed with the tabs 15. In this case, a liquid-permeable material will be used as the second web 60 and the backsheet 3 will be configured in conformity with the topsheet 2 shown in FIG. 1.

Figure 3:
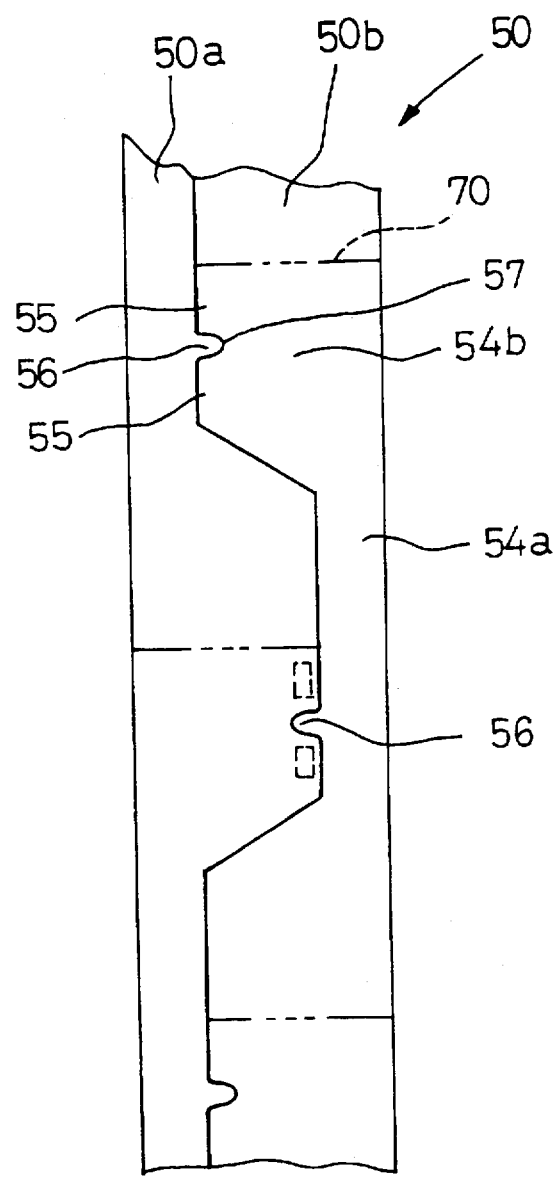
FIG. 3 is a diagram similar to FIG. 2(1) illustrating an embodiment of the invention.

FIG. 3 is a plan view showing the first and second continuous webs 50a, 50b according to another embodiment of the invention which are of configurations different from those shown in FIG. 2. The webs 50a, 50b have the second convex edge portions 55 formed above and below the respective convex edge portions 54b by partially cutting away at 57 these convex edge portions 54b and the concave edge portions 54a are in turn formed with the convex edge portions 56 corresponding to those cutouts.

Figure 4:
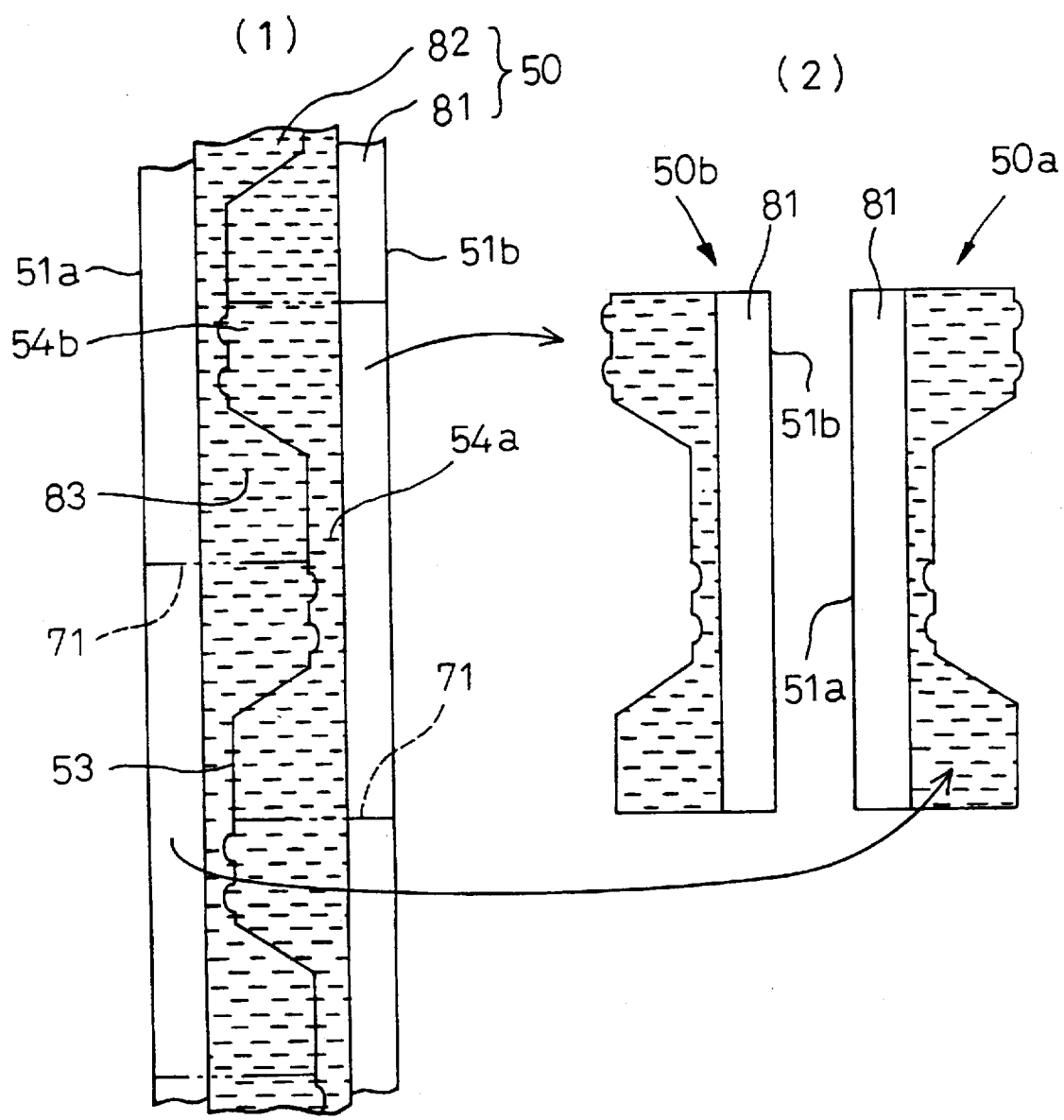
FIG. 4 is a diagram similar to FIG. 2 illustrating still another embodiment of the invention.

FIG. 4 is a view similar to FIG. 2 illustrating still another embodiment of the invention. The first web 50 shown in FIG. 4(1) comprises a laminate of a relatively wide underlying web 81 and a relatively narrow overlying web 82, both webs 81, 82 being integrated by a plurality of bonding lines 83 intermittently extending in the transverse direction and parallel to one another in the longitudinal direction. The first web 50 is cut along the cutting line 53 and the second cutting line 71 and mutually aligned to be the first and second partial webs 50a, 50b as shown in FIG. 4(2). These webs 50a, 50b are bonded to the second web 60 (not shown) along portions of the underlying web 81 extending outward beyond the respective inner side edges of the overlying web 82 to obtain the composite backsheet 3 or composite topsheet. In the case of the composite topsheet, a liquid-permeable material may be used as the underlying web 81 while a liquid-impermeable material may be used as the overlying web 82 to assure that body fluids can smoothly permeate the liquid-absorbent core 4 even when the upper surface of the liquid-absorbent core 4 is covered with the underlying web 81. When both the underlying web 81 and the overlying web 82 are fibrous webs comprising individual fibers oriented in the longitudinal direction, these webs may be integrated by the transversely long bonding lines as shown to improve a tensile strength of these webs in the transverse direction. The presence of these bonding lines does not unacceptably increase a rigidity of the first web 50, since these bonding lines are spaced one from another transversely as well as longitudinally of these webs 81, 82.

It is possible without departing from the scope of the invention to replace each adhesive fastening region 16 by one component of the paired plane fastener known under the trade name of Velcro and to attach the other component of such plane fastener to the outer surface of the front section 6 at a given location. Bonding of the respective components of the diaper 1 may be achieved by means of adhesive such as hot melt adhesive or by heat-sealing technique so far as the heat-sealable components are concerned.

The inventive method for making components of undergarment allows the manufacturing cost of undergarment to be effectively reduced by eliminating a need for any separate members to form the tabs facilitating the undergarment to be fastened or released at the fastening regions and, in addition, a need for relatively large-sized base tape of the fasteners as has conventionally been required by the prior art, because the tabs can be formed merely by partially cutting away the side edges of the crotch section.

What is claimed is:

1. A method for making components of an undergarment comprising steps of subjecting a first continuous web having side edges to cutting in a longitudinal direction along an alternative concave-convex cutting line between said side edges to thereby form a first partial web and second partial web that each has a series of alternating concave edge portions and a series of alternating convex edge portions, longitudinally shifting the first partial web relative to the second partial web by a predetermined pitch so that the concave and convex edge portions of the first partial web are exactly aligned with the corresponding concave and convex edge portions of the second partial web, respectively, and bonding outer edges of these first and second partial webs remote from their concave and convex edge portions to respective outer edges of a second continuous web to form a composite web, said method being characterized in that said method further comprises steps of utilizing said cutting line to form in said concave and convex edge portions of said first and second partial webs second concave and convex edge portions which are able to be respectively aligned simultaneously as said first and second partial webs are aligned to each other and smaller than the first-mentioned concave and convex edge portions; and forming fastening regions used to fasten said undergarment around the wearer's waist on and/or adjacent said second convex edge portions.

2. A method as defined by claim 1, wherein said undergarment is a disposable diaper whereas said second web is adapted to be used as a topsheet of said diaper, said first and second partial webs being bonded to transversely opposite sides of said topsheet.

3. A method as defined by claim 1, wherein said undergarment is a disposable diaper whereas said second web is adapted to be used as a backsheet of said diaper, said first and second partial webs being bonded to transversely opposite sides of said backsheet.

4. A method as defined by claim 1, wherein said second convex edge portions define tabs operatively associated with the fastening regions formed on side edges of the front or rear section of said undergarment.

* * * * *